(12) United States Patent
Mandel et al.

(10) Patent No.: US 12,196,826 B2
(45) Date of Patent: Jan. 14, 2025

(54) METHOD FOR DETECTING AND/OR IDENTIFYING MAGNETIC SUPRAPARTICLES USING MAGNET PARTICLE SPECTROSCOPY OR MAGNET PARTICLE IMAGING

(71) Applicants: FRAUNHOFER-GESELLSCHAFT ZUR FÖRDERUNG DER ANGEWANDTEN FORSCHUNG E. V., Munich (DE); JULIUS-MAXIMILIANS-UNIVERSITÄT WÜRZBURG, Würzburg (DE)

(72) Inventors: Karl-Sebastian Mandel, Würzburg (DE); Stephan Müssig, Würzburg (DE); Susanne Wintzheimer, Würzburg (DE); Florian Fidler, Erlangen (DE); Daniel Haddad, Erlangen (DE); Karl-Heinz Hiller, Erlangen (DE)

(73) Assignees: Fraunhofer-Gesellschaft zur förderung der angewandten Forschung e.V., Munich (DE); Julius-Maximilians-Universität Würzburg, Würzburg (DE)

( * ) Notice: Subject to any disclaimer, the term of this patent is extended or adjusted under 35 U.S.C. 154(b) by 549 days.

(21) Appl. No.: 17/598,365

(22) PCT Filed: Mar. 24, 2020

(86) PCT No.: PCT/EP2020/058135
§ 371 (c)(1),
(2) Date: Sep. 27, 2021

(87) PCT Pub. No.: WO2020/200911
PCT Pub. Date: Oct. 8, 2020

(65) Prior Publication Data
US 2022/0187390 A1   Jun. 16, 2022

(30) Foreign Application Priority Data

Mar. 29, 2019 (DE) ..................... 10 2019 204 483.2

(51) Int. Cl.
*G01R 33/12* (2006.01)
*G01N 27/72* (2006.01)

(52) U.S. Cl.
CPC ......... *G01R 33/1276* (2013.01); *G01N 27/72* (2013.01)

(58) Field of Classification Search
CPC .... G01R 33/1276; G01N 27/72; B42D 25/28; B42D 25/369; B42D 25/41; A61B 5/0515
See application file for complete search history.

(56) References Cited

U.S. PATENT DOCUMENTS

| 8,021,517 B2 | 9/2011 | Hughes et al. |
| 2011/0182821 A1* | 7/2011 | Gruell ..................... B82Y 5/00 264/108 |

(Continued)

FOREIGN PATENT DOCUMENTS

| CN | 103468056 A | 12/2013 |
| CN | 103774502 A | 5/2014 |

(Continued)

OTHER PUBLICATIONS

Supattarasakda, et al., Control of hematite nanoparticle size and shape by the chemical precipitation method, Powder Technology, vol. 249, 2013, pp. 353-359 (Year: 2013).*

(Continued)

*Primary Examiner* — Daniel R Miller
(74) *Attorney, Agent, or Firm* — Leydig, Voit & Mayer, Ltd.

(57) ABSTRACT

The invention relates to a method for detecting and/or identifying magnetic supraparticles using magnet particle spectroscopy (MPS) or magnet particle imaging (MPI), (Continued)

wherein magnetic supraparticles are provided, each of which contains a plurality of magnetic nanoparticles and which have a specific composition and/or structure. The magnetic supraparticles are exposed to at least one magnetic field, whereby at least one voltage and/or a voltage curve is induced based on the magnetic moment of the magnetic supraparticles. The at least one voltage and/or the voltage curve is detected as at least one measurement signal, and at least one spectrum is generated from the at least one measurement signal, said spectrum containing harmonics, each of which has an amplitude and a phase. The magnetic supraparticles are (uniquely) detected and/or identified using the at least one generated spectrum.

19 Claims, 7 Drawing Sheets

(56) References Cited

U.S. PATENT DOCUMENTS

| 2012/0319030 | A1 | 12/2012 | Cho |
| 2013/0243699 | A1 | 9/2013 | Wang et al. |
| 2015/0165070 | A1 | 6/2015 | Kratz et al. |
| 2015/0367380 | A1 | 12/2015 | Kotov et al. |
| 2017/0067972 | A1 | 3/2017 | Diamond et al. |
| 2018/0293411 | A1 | 10/2018 | Becker |

FOREIGN PATENT DOCUMENTS

| DE | 102010011936 A1 * | 9/2011 | ............ G01N 27/72 |
| DE | 102012201774 A1 | 8/2013 | |
| DE | 102014110573 A1 | 1/2016 | |
| DE | 102015108749 A1 | 12/2016 | |
| DE | 102015109637 A1 | 12/2016 | |
| DE | 102015118816 A1 | 5/2017 | |
| WO | 2012/001579 A1 | 1/2012 | |
| WO | 2012/034696 A1 | 12/2016 | |
| WO | 2018/144599 A1 | 8/2018 | |

OTHER PUBLICATIONS

Duak et al., Controlled heteroaggregation of two types of nanoparticles in an aqueous suspension, Journal of Colloid and Interface Science, vol. 438, 2015, pp. 235-243 (Year: 2015).*

Wagner et al., Towards nanoscale composite particles of dual complexity, Journal of Colloid and Interface Science, vol. 355, Issue 1, 2011 (Year: 2011).*

Bao et al., Self-assembly of superparamagnetic nanoparticles, J. Mater. Res., vol. 26, No. 2, Jan. 28, 2011 (Year: 2011).*

Mi, et al., A Micro/Nano Composite for Combination Treatment of Melanoma Lung Metastasis. Adv. Healthcare Mater. 2016, 5, 936-946 (Year: 2016).*

Biederer et al., "Magnetization response spectroscopy of superparamagnetic nanoparticles for magnetic particle imaging," *J. Phys. D: Appl. Phys*. 42(20): 205007 (2009).

Lüdtke-Buzug et al., "Characterization of Iron-Oxide Loaded Adult Stem Cells for Magnetic Particle Imaging in Targeted Cancer Therapy," 8th *International Conference on the Scientific and Clinical Applications of Magnetic Carriers 1311*: 244-248, May 25-29, 2010, Rostock, Germany.

Wawrzik et al., "Multivariate Magnetic Particle Spectroscopy for Magnetic Nanoparticle Characterization," 8th *International Conference on the Scientific and Clinical Applications of Magnetic Carriers 1311*: 267-270, May 25-29, 2010, Rostock, Germany.

Wintzheimer et al., "Supraparticles: Functionality from Uniform Structural Motifs," *ACS Nano* 12(6): 5093-5120 (2018).

German Patent Office, Office Action in German Patent Application No. 10 2019 204 483.2 (Jan. 22, 2020).

European Patent Office, International Search Report in International Application No. PCT/EP2020/058135 (Jun. 26, 2020).

European Patent Office, Written Opinion in International Application No. PCT/EP2020/058135 (Jun. 26, 2020).

International Bureau of WIPO, International Preliminary Report on Patentability in International Application No. PCT/EP2020/058135 (Sep. 28, 2021).

* cited by examiner

METHOD FOR DETECTING AND/OR IDENTIFYING MAGNETIC SUPRAPARTICLES USING MAGNET PARTICLE SPECTROSCOPY OR MAGNET PARTICLE IMAGING

CROSS-REFERENCE TO RELATED APPLICATIONS

This patent application is the U.S. national phase of International Application No. PCT/EP2020/058135, filed on Mar. 24, 2020, which claims the benefit of German Patent Application No. 10 2019 204 483.2, filed Mar. 29, 2019, the disclosures of which are incorporated herein by reference in their entireties for all purposes.

The present invention relates to a method for the detection and/or identification of magnetic supraparticles by means of magnetic particle spectroscopy (MPS) or magnetic particle imaging (MPI) in which magnetic supraparticles are provided that each contain a plurality of magnetic nanoparticles and comprise a specific composition and/or structure, in which the magnetic supraparticles are exposed to at least one magnetic field, whereby at least one voltage and/or one voltage progression is induced in dependence on the magnetic moment of the magnetic supraparticles, wherein the at least one voltage and/or voltage progression is detected as at least one measurement signal, at least one spectrum is generated from the at least one measurement signal, which spectrum contains higher harmonics that each have an amplitude and a phase, and the magnetic supraparticles are (unambiguously) detected and/or identified with reference to the at least one generated spectrum. The present invention additionally also relates to the use of the method in accordance with the invention for the detection and/or identification of objects.

Almost all products are today characterized by huge complexity with respect to their production logistics. Global supply sources for raw materials, semifinished products, and components are the rule and apply to almost all goods, from domestic appliances and clothing up to high-end electric devices, vehicles, or pharmaceutical products.

The warranty requirement of the final manufacturer requires a complete record of the starting materials and intermediate products in the supply chain, either for technical, legal, or (geo)political reasons. Original components additionally have to be distinctively marked to prevent product piracy. Damages due to counterfeits thus amount to more than €50 bn in Germany alone. Counterfeit or falsified products can in particular be life-threatening in the pharmaceutical sector. An EU regulation therefore provides that medicines have to be securely marked by 2019.

In addition to the passive proof of origin, it is becoming increasingly more important to assign an active, communicable identifier to every object to support digitization and automation in production routines (Industry 4.0).

For the purposes of sustainability, the second-life sector up to the recycling of components and secondary raw materials also has to be considered beyond the actual product life. To close the circle ("cradle-to-cradle") a marking is therefore necessary that is equally indestructible and unique.

For the named reasons, it is of very great interest to develop inexpensive and reliable techniques for the marking of objects that satisfy all these demands. The previously existing solution approaches are restricted with respect to their miniaturization capability and universal applicability in all the desired material or product components.

Physical effects of nanoscalability, however, enable a particle based object marking to be able to address the four features of auditability, traceability, sustainability, counterfeit protection and to be able to satisfy the large variety of demands.

Contrast agents for an improved imaging, inter alia in computed tomography (CT) or magnetic resonance tomography (MRT), are of particular importance in modern medicine. Multimodal contrast agents are being intensely researched that are often based on nanoparticles. Studies on complex particles, built up of nanoparticles having different physical signaling behavior or signal influencing behavior are known from this research field.

A plurality of marking features have been developed over the past decades that focus on fake/falsification protection, for example watermarks, hologram techniques, IR protective colors, metal safety strips, or in recent times the RFID technology. The latter is also of great importance in the sense of Industry 4.0. The great disadvantage of all the previously existing transmitters is, however, that they typically have sizes in the millimeter range and can as a rule only be applied to surfaces so that it is not possible to speak of a real integration of the marker/a "direct" marking of an object here. The same applies to practically all the established markers. If markers are large and can only be applied to surfaces, they are, however, easy to remove or to destroy.

The idea of using particles as product markers has already been pursued in some research studies. The focus was on graphical or optical features in studies from the last 15 years. With graphical features, a sequence of structures is spatially visualized; for example, dyed polymer layers or metal nanowires divided into strips. With optical features, organic dyestuffs are typically embedded in particles that act as carriers. The approach has furthermore been pursued of embedding fluorescent quantum dots (QDs, e.g., CdSe) in polystyrene particles and to obtain characteristic optical spectra by mixtures of different particles. It has become possible here to produce composite particles (secondary structure from different nanomodules) with unique optical codes. The potential toxicity of QDs is disadvantageous.

The approach is already known from the prior art of marking objects with luminescent particle systems such as QDs, doped nanodiamonds, or plasmon active particles (see e.g., U.S. Pat. No. 8,021,517 B2). There are additionally magnetic particles in connection with biomedical applications (see e.g., US 2012/0319030 A1) that have multifunctionality that is as a rule achieved by a combination with fluorescent particles.

Magnetic particle imaging (MPI) is also known from the field of biomedical imaging. In this connection, the production of magnetic nanoparticles for use as imaging markers or tracers, detectable by MPI, is described in WO 2012/001579 A1. Reference is in part also made to the measurement by means of MPS in this connection since it is the 0-dimensional spectroscopic method of MPI and is thus closely related to it. However, only simple nanoparticles are used in WO 2012 001579 A1.

Approaches are furthermore known in which magnetic particles are applied to objects, in particular valuable papers, in different manners (as ink, for example). Marking then either takes place by the simple detection of this magnetic signal (see e.g., CN 103774502 A) or in that the magnetic material is applied in a defined arrangement (see e.g., CN 103468056 A) so that a graphical marking additionally thereby results. The application of the magnetic material in a specific pattern is in part expanded by a variation of the magnetic properties; for example, hard magnetic or soft magnetic, ferromagnetic or non-ferromagnetic, or similar, as described in US 2018/293411 A.

In addition various systems are known from the prior art such as luminescent zinc oxide particles as photostimulable nanoparticle markers and multifunctional nanoparticle inks having characteristic magnetic, optical, and electrical marker features.

The assembly of nanoparticles into composite particles such as magnetic composite particles, magnetic composite particles having luminescent, degradable metal organic framework links, or magneto-optical rods are moreover known from DE 10 2012 201 774 A1, DE 10 2015 109 637 A1, and DE 2015 118 816 A1. A use of these particles as encoding objects in an identification or detection process is, however, not proposed.

DE 10 2015 108 749 A1, WO 2012/034696 A1, and DE 10 2014 110573 finally deal with particles having characteristic signals, usable as markers. The particles used there are, however, only simple nanoparticles. In addition, the use of magnetic particle spectography is not proposed.

Starting from this, it was the object of the present invention to provide a method for a simple and exact detection and/or identification of particles.

This object is achieved by the features of the method described herein and by the use of the method described herein. Advantageous developments are also described.

DETAILED DESCRIPTION OF THE INVENTION

Figure 1:
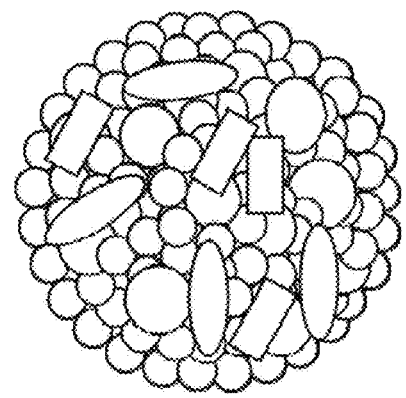
FIG. 1 illustrates an exemplary magnetic supraparticle that can be used in an aspect of the invention and contains a plurality of magnetic nanoparticles having different sizes and shapes.

In accordance with the invention, a method is thus provided for the detection and/or identification of magnetic supraparticles by means of magnetic particle spectroscopy or magnetic particle imaging in which
a) magnetic supraparticles are provided that each contain a plurality of magnetic nanoparticles and have a specific composition and/or structure;
b) the magnetic supraparticles are exposed to at least one magnetic field, whereby at least one voltage and/or voltage progression is/are induced in dependence on the magnetic moment of the magnetic supraparticles, wherein the at least one voltage and/or the voltage progression is detected as at least one measurement signal,
c) at least one spectrum is generated from said at least one measurement signal, which spectrum contains higher harmonics that each have an amplitude and a phase; and
d) the magnetic supraparticles are detected and/or identified with reference to or on the basis of the at least one generated spectrum.

In the method in accordance with the invention, magnetic particle spectroscopy (MPS) or magnetic particle imaging (MPI) is thus used to unambiguously detect and/or identify magnetic supraparticles. The magnetic supraparticles can be integrated in objects here. The objects themselves can thus also be detected or identified by detection/identification of the magnetic supraparticles integrated in the objects. The method in accordance with the invention can thus be used for the detection and/or identification of objects.

In step a) of the method in accordance with the invention, magnetic supraparticles are first provided that each contain a plurality of magnetic nanoparticles and have a specific composition and/or structure. Supraparticles are here generally understood as particles that are each built up of smaller particles. The supraparticles can, for example, be microparticles that are each built up of nanoparticles. In accordance with the invention, the supraparticles provided in step a) contain a plurality of magnetic nanoparticles. The supraparticles are consequently magnetic supraparticles. The magnetic supraparticles have a magnetic moment. In addition, the magnetic supraparticles have a specific (i.e., a predetermined or defined or known) composition and/or structure. The used composition and/or structure of the supraparticles can thus ultimately be selected as desired. It is, however, decisive that it is a clearly defined and thus known composition and/or structure. A composition is here preferably also understood as a defined quantity ratio of the nanoparticles from which the supraparticles are built up. The structure of the magnetic supraparticles is here understood as the structural arrangement of the components of the composition of the magnetic supraparticles. The composition and structure of the magnetic supraparticles influence their magnetic properties, i.e., also their magnetic moment and their magnetization behavior. Magnetic supraparticles having a specific composition and/or structure thus have characteristic magnetic properties that can be determined with the aid of suitable determination methods such as magnetic particle spectroscopy or magnetic particle imaging.

In step b) of the method in accordance with the invention, the magnetic supraparticles provided in step a) are exposed to at least one magnetic field. At least one voltage and/or a voltage progression is/are induced in dependence on the magnetic moment of the magnetic supraparticles by the exposure to the at least one magnetic field. This at least one induced voltage and/or this at least one induced voltage progression is/are then detected as at least one measurement signal. Due to the specific composition and/or structure of the magnetic supraparticles, they have a characteristic magnetic moment so that a voltage characteristic for the magnetic supraparticles used or a voltage progression characteristic for the magnetic supraparticles used is/are induced and thus a measurement signal characteristic for the magnetic supraparticles used is also generated and detected in step b). In the step, the magnetic supraparticles can be exposed to different magnetic fields, with these being able to be different static and/or time dependent magnetic fields, for example.

For example, the magnetic supraparticles are exposed to a magnetic field in step b), whereby a voltage is induced in dependence on the magnetic moment of the magnetic supraparticles that is detected as a measurement signal.

In step c) of the method in accordance with the invention, at least one spectrum is generated from the at least one measurement signal detected in step b). This at least one spectrum contains higher harmonics that have an amplitude and a phase. The generation of the at least one spectrum preferably takes place by means of Fourier transformation. The at least one measurement signal characteristic for the used magnetic supraparticles detected in step b) is thus converted within step c) into at least one spectrum characteristic for the used magnetic supraparticles. This at least one spectrum contains higher harmonics that are characteristic for the used magnetic supraparticles.

Steps b) and c) can also be repeated once or several times, with the magnetic supraparticles each being able to be exposed to a different magnetic field in the different steps b). As a consequence, a separate measurement signal for every single one of the steps b) carried out is obtained from which then a respective separate spectrum is generated in the respective step c). The magnetic fields used in the different steps b) can, for example, be different static and/or time dependent magnetic fields.

In step d), finally, the magnetic supraparticles are detected and/or identified with reference to the at least one spectrum generated in step c) (or the spectra generated in a plurality of steps c). A conclusion can be drawn on the special magnetic supraparticles used in step a) due to the higher harmonics of the spectrum characteristic for the magnetic supraparticles used. In other words, the magnetic supraparticles used can be detected and/or identified, for example, with reference to the higher harmonics in the spectrum characteristic for these particles.

In the method in accordance with the invention, use is thus made of the fact that magnetic supraparticles having a specific composition and/or structure have characteristic magnetic properties that, for example, result in characteristic higher harmonics in a spectrum measured by means of magnetic particle spectroscopy (MPS) or by means of magnetic particle imaging (MPI), with reference to which the used magnetic supraparticles can be detected and/or identified. It is thus important for the method in accordance with the invention that the magnetic supraparticles provided in step a) have a specific, known composition and/or structure. The magnetic supraparticle can, for example, comprise a plurality of different types of nanoparticles that differ from one another in their shape and/or size. These nanoparticle types can be present in a specific quantity ratio to one another so that a specific composition of the supraparticle results and can be present in a specific structural arrangement with respect to one another so that a specific structure of the supraparticle results. In this manner, the composition and/or structure of the magnetic supraparticles can be fixed such that a specific characteristic spectrum or a series of specific characteristic spectra can be obtained by means of magnetic particle spectroscopy or magnetic particle imaging. In other words, a type of "fingerprint" or "ID" or (unique) "code" can be set for the supraparticles by fixing the composition and/or structure, with this "fingerprint" or this "ID" or this (unique) "code" being able to be detected and/or identified by the measurement by means of magnetic particle spectroscopy or magnetic particle imaging or with reference to the higher harmonics of the at least one spectrum obtained there. A conclusion can thus be drawn on the fixed composition and/or structure with reference to the at least one obtained spectrum, whereby a detection and/or identification of the magnetic supraparticles used is made possible. The "fingerprint" or "ID" or "code" of the magnetic supraparticle can, for example, be stored in a database or in a code table so that a simpler detection and/or identification of the specific magnetic supraparticles is made possible by a comparison of the measured "fingerprint" or "ID" or "code" with the "fingerprint" or "ID" or "code" from the database or the code table.

The composition or structure of the particles can preferably be fixed such that a plurality of different "fingerprints" or "IDs" or "coded" can be set for the particles that are then unambiguously identifiable by means of MPS or MPI. In other words, different types of supraparticles can be used that each have a separate specific composition and/or structure and thus each have their own "fingerprint" or own "ID" or own "code". These "fingerprints" or "IDs" or "codes" can be stored in a database or in a code table so that the measured "fingerprint" or the measured "ID" or the measured "code" only has to be compared with the different "fingerprints" or "IDs" or "codes" from the database or code table for the detection and/or identification of the specific magnetic supraparticles.

In the present invention, special magnetic particles are unambiguously identified by their composition or structure by means of the technique of magnetic particle spectroscopy or magnetic particle imaging. Magnetic particle spectroscopy is also known under the names "Magnetization Response Spectroscopy" (see S. Biederer, T. Knopp, T. Sattel, K. Lüdtke-Buzug, B. Gleich, J. Weizenecker, J. Borgert, T. Buzug, J. Phys. D: Appl. Phys., 2009, 42, 205007), "Magnetic Particle Spectrometry" (MPS) (see K. Lüdtke-Buzug, D. Rapoport, D.

Schneider: "Characterization of Iron-Oxide Loaded Adult Stem Cells for Magnetic Particle Imaging in Targeted Cancer Therapy", AIP conf Proc, 2010, 1311, 244-248), and "Magnetic Particle Spectroscopy" (MPS) (see T. Wawrzik, F. Ludwig, M. Schilling: "Multivariate Magnetic Particle Spectroscopy for Magnetic Nanoparticle Characterization, $8^{th}$ international conference on the scientific and clinical applications of magnetic carriers, 2010, 1311, 267-270).

Magnetic particle imaging (MPI) is closely related to magnetic particle spectroscopy. In comparison with MPI, local information of the measured signal is additionally determined and thus the "spectral" information obtained in the MPS is associated with a respective specific location.

MPS or MPI is an approach that provides the suitable analysis technique to be able to detect complex particles with a magnetic ID for the first time. The technology of MPS or MPI is able to detect a characteristic spectrum from the integral interplay of magnetic nanocomponents and their structural arrangement. This takes place contactlessly, with depth effect, and within a few milliseconds.

The measurement principle of MPS or MPI is based on the fact that a magnetic sample is exposed to a magnetic alternating field and the magnetization of the sample following this alternating field is recorded. The magnetization resulting with superparamagnetic and ferro/ferrimagnetic particles and the signal resulting therefrom are non-linear to the progression of the field applied. A spectrum that shows characteristic higher harmonics is obtained by Fourier transformation of the measurement signal (magnetization response).

The basic measurement principle of the measurement method of magnetic particle spectroscopy or magnetic particle imaging used will be explained in the following:

A sample is exposed to a magnetic alternating field, with the magnetic moment of the sample following the external alternating field. A voltage is induced by this change of the magnetic flux that can be detected by a suitable measurement structure. Since the magnetization behavior of superparamagnetic, ferromagnetic, and ferrimagnetic materials is non-linear to the outer field, a spectrum is generated on the Fourier transformation of the measurement signal that contains higher harmonics. The higher harmonics have an amplitude and a phase. Both the amplitude and the phase of one or more higher harmonics can be used as a characteristic signal. The signal generation can take place by an arbitrary setting of measurement parameters. The frequency of the applied magnetic field, the magnetic field power, the measurement duration, or the number of measurements at the measurement device can thus vary, for example. A plurality of measurements having variable measurement parameters for the signal detection are thus also conceivable and preferably provided.

If suitable particles are used, the signals can be influenced and set both via measurement parameters and via physical or chemical particle parameters so that the measurement signals can be used as a "code" or as an "ID". In the method in accordance with the invention, the code reading can preferably take place with the relative amplitude intensity and not with the absolute measurement values. This can take place by a characteristic progression of the amplitude intensity in dependence on the higher harmonics. In this process, one, two, or more amplitude intensities of different higher harmonics can be put in relationship so that the drop or rise of the curves is described. A graph curve can thereby be exactly described by a skillful mathematical process. Code particles can be identified by an inclusion of errors and preferably by a comparison, e.g., with a database or a code table, in which the code signals are stored. Additionally or alternatively, absolute values or relative values of the phase of one or more higher harmonics can be used. It is conceivable that with different samples, an amplitude progression occurs that is identical within the framework of the error, but the phase differs in dependence on the higher harmonics, or vice versa. The amplitude intensity and phase that are measured by means of MPS or MPI are dependent on a complex interplay of different material properties.

Magnetic particles have the property that they are detectable far below the visible range of the electromagnetic spectrum. This has the great advantage that it is thus possible to be able to read the particles from the bulk matrix of an optically non-transparent material. This means that the particles can be integrated in a material and do not have to be applied to the surface, which means, on the one hand, that the particles are protected from destruction, cannot be easily removed, and are real, hidden features that are not obviously (visually) recognizable from the outside.

Due to the use of magnetic supraparticles that contain magnetic nanoparticles and have a specific composition and/or structure and due to the use of magnetic particle spectroscopy or magnetic particle imaging, a method for a simple and exact detection and/or identification of particles is thus obtained that can be used for a simple and exact detection and/or identification of objects.

The manufacture of the magnetic supraparticles provided in step a) can preferably take place by means of spray drying. The magnetic nanoparticles are assembled into the magnetic supraparticles in this process. The magnetic nanoparticles can, for example, be sprayed in dispersion by means of an atomization nozzle as fine (1 μm to 10 μm) droplets into a chamber in which an increased temperature is present, whereupon the solvent (preferably water) evaporates and the magnetic nanoparticles agglomerate into the magnetic supraparticles.

In addition to this preferred manufacturing method, the magnetic nanoparticles can, however, be manufactured in accordance with a different method known to the skilled person; for example, in accordance with a method selected from the group consisting of emulsion methods, sol-gel methods, microfluidic methods, dry self-assembly methods, wet self-assembly methods, self-limited self-assembly methods, and combinations thereof.

An explanation of the most important methods for the manufacture of the magnetic supraparticle can be found in S. Wintzheimer, T. Granath, M. Oppmann, T. Kister, T. Thai, T. Kraus, N. Vogel, K. Mandel, "Supraparticles: Functionality from Uniform Structural Motifs", ACS Nano, 2018, 12, 6, 5093-5120.

Nanoparticles are understood in accordance with the invention as particles having a particle size from 0.1 nm to 1000 nm, preferably from 1 nm to 100 nm.

The magnetic supraparticles are preferably magnetic microparticles and/or magnetic nanoparticles. A microparticle is here understood as a particle having a particle size of 0.1 μm to 1000 μm, preferably of 1 μm to 100 μm.

Within the framework of the present application, the particle size of the magnetic supraparticles and/or of the nanoparticles contained in the magnetic supraparticles can be determined, for example, by light microscopy, electron microscopy, dynamic light scatter, or Fraunhofer diffraction.

A preferred variant of the method in accordance with the invention is characterized in that the detection and/or identification of the magnetic supraparticles in step d) takes place with reference to the progression of the phases of the higher harmonics of the at least one spectrum and/or with reference to relative relationships of intensities of the amplitude of the higher harmonics of the at least one spectrum. The magnetic supraparticles that contain a plurality of magnetic nanoparticles have a magnetization behavior in the applied alternating field or magnetic field that results in a characteristic curve progression of the amplitude intensities and/or of the phase of the "higher order harmonics" of the magnetic spectrum, measured by means of MPS or MPI due to the interaction of the components or their structural orientation. It is of advantage here that the progression of the phase and the relative amplitude relationships of specific higher harmonics with respect to one another are characteristic for the used magnetic supraparticles with their determined composition and/or structure and this relationship of the intensities can thus be unambiguously associated with the specific supraparticles used. It must be noted here that, due to the observation of the relative relationships of the intensities, the system is practically independent of environmental effects that may influence the absolute intensity of the magnetic signal of the particle.

A further preferred variant of the method in accordance with the invention is characterized in that
the magnetic supraparticles each have a particle size of 50 nm to 150 μm, preferably from 1 μm to 10 μm; and/or
the magnetic nanoparticles of the plurality of magnetic nanoparticles each have a particle size of 1 nm to 100 nm.

The nanoparticles of the plurality of magnetic nanoparticles can all (substantially) have the same particle size. The nanoparticles, however, preferably have different particle sizes; for example, at least two different particle sizes or at least three different particle sizes, or at least four different particle sizes. The particle size of the nanoparticles influences the magnetic properties or the magnetic moment of the supraparticles. The more different particle sizes the nanoparticles have from which the supraparticles are built up, the more characteristic, distinguishable spectra can be generated, which increases the number of available "codes".

In accordance with a preferred embodiment, the magnetic nanoparticles of the plurality of magnetic nanoparticles each have a basic shape that is selected from a spherical basic shape, an octahedral basic shape, an ellipsoid basic shape, a rod-shaped basic shape, a cylindrical basic shape, and a cubic basic shape. The nanoparticles of the plurality of magnetic nanoparticles can all have the same basic shape. However, the nanoparticles preferably have different basic shapes, for example at least two different basic shapes or at least three different basic shapes, or at least four different basic shapes. The basic shape of the nanoparticles influences the magnetic properties or the magnetic moment of the supraparticles. The more different basic shapes the nanoparticles have from which the supraparticles are built up, the more characteristic, distinguishable spectra can be generated, which increases the number of available "codes".

It is further preferred that the nanoparticles of the plurality of magnetic nanoparticles each comprise or consist of a material that is selected from the group consisting of ferromagnetic materials, ferrimagnetic materials, superparamagnetic materials, and mixtures thereof. The material is particularly preferably selected from the group consisting of iron oxides, ferrites, and mixtures thereof. These are advantageously particularly inexpensive and environmentally compatible and additionally only have small toxicity.

A further preferred variant of the method in accordance with the invention is characterized in that the plurality of magnetic nanoparticles comprise a plurality of types, preferably at least three types, particularly preferably at least four types, of magnetic nanoparticles
that differ from one another at least in their particle sizes; and/or
that differ from one another at least in their basic shapes, with the basic shape preferably being selected from a spherical basic shape, an octahedral basic shape, an ellipsoid basic shape, a rod-shaped basic shape, a cylindrical basic shape, and a cubic basic shape; and/or
that differ from one another at least in their material.

If the nanoparticles have different particle sizes and/or basic shapes and/or materials, more characteristic, distinguishable spectra can be generated, which increases the number of available "codes".

A further preferred variant of the method in accordance with the invention is characterized in that the magnetic supraparticles or at least some of the magnetic supraparticles are hollow spheres. Hollow spheres are here understood as a special structure of the supraparticles in which the supraparticles only comprise a hollow shell, but no core arranged within this shell. The shell here preferably has a thickness of 0.25 μm to 2 μm. The hollow region arranged within the shell preferably has a diameter of 5 μm to 100 μm. The hollow spheres used have the advantage that, for example, their structure can easily be modified by mechanical pressure or shear forces on the hollow spheres. Since the structure of the hollow spheres, however, has a direct influence on the received measurement signal of the MPS or MPI measurements, a conclusion can thus be directly drawn on the, for example mechanical, influence on the hollow spheres from the recorded measurement signal. The hollow spheres therefore act as a detector for mechanical influences, for example. A "storage effect" moreover additionally results from the irreversible change of the structure of the hollow sphere, i.e., mechanical effects or shear forces that have acted on the hollow spheres prior to the actual MPS or MPI measurement and that have changed their structure in so doing are detected and read in the later measurements. In addition, the mechanical properties of the hollow spheres can be coordinated exactly and very finely, for example, by setting the wall thickness and strength of the shell or by a variation of the nanoparticles used. It is thus possible to manufacture a respective detector that is adapted to the mechanical influences to be expected and that is, for example, only deformed from a certain force effect onward and does not detect smaller vibrations during transport, for example. A further preferred variant of the method in accordance with the invention is characterized in that the plurality of magnetic nanoparticles comprise at least two, preferably at least three, types of magnetic nanoparticles that differ from one another at least in their saturation magnetization and in that a static or time variable offset field is additionally applied within step b).

This preferred variant—called measurement approach 2 in the following—represents a supplement to the basic measurement approach—called measurement approach 1 in the following—of the method in accordance with the invention. An even more exact detection or identification of the magnetic supraparticles can be achieved in this manner. If, for example, three magnetic particle types X, Y, and Z that differ considerably in their saturation magnetization are interassociated in a magnetic supraparticle, a system is available whose composition X-Y-Z is detectable. For this purpose, the strength of the applied magnetics alternating field is varied during the measurement of the X-Y-Z component particle such that on a first measurement, the field as an offset is always at least so strong that particle type P permanently achieves its magnetic saturation. In a second measurement, the field strength is selected such that type X and now also type Y are in saturation. In a third measurement, the field strength is so weak that none of the three magnetic particle types are in saturation. The component that is respectively saturated no longer follows the magnetic alternating field and is thus deactivated as a signal transmitter. A combination signal of first Y+Z, then only Z, and then X+Y+Z is thus obtained in the three measurements. The respective signal spectra correlate with the respective (quantitative) portions of the components X, Y, and Z that can be freely set. A unique ID for the multicomponent particles can thus be generated.

In principle, any desired number of magnetic particle types is possible to build up the multicomponent particles having IDs of different complexities. This offset field can either be varied between successive measurements or continuously during one measurement, e.g., by a linear increase of this offset field.

A further preferred variant of the method in accordance with the invention is characterized in that the plurality of magnetic nanoparticles comprise at least two, preferably at least three, types of magnetic nanoparticles that differ from one another at least in their (non-linear) magnetization behavior in an applied magnetic field and/or in their saturation magnetization and in that the magnetic field strength of the magnetic field and/or the frequency of the magnetic field is/are varied within step b).

This preferred variant—called measurement approach 3 in the following—represents a further supplement to the basic measurement approach (i.e., measurement approach 1) of the method in accordance with the invention. If, for example, three magnetic particle types X, Y, and Z that are interassociated into a magnetic supraparticle either in their saturation magnetization and/or in their (nonlinear) magnetization behavior with respect to the applied magnetic field, the composition of the system thus created can, analogously to the previously described measurement approach 2, be used by a variation of the magnetic alternating field used for the measurement. This variation comprises the change of the strength of this field; a change of the frequency or a combination of the two is equally possible. These variations can be polled either in successive measurements or in a continuously changing magnetic field as a measurement signal.

If the particle X, analogously to measurement approach 2, for example, shows a low saturation magnetization and thus a non-linear behavior above all at low magnetic field strengths, the measurement signal can only be varied a little by an increase in the field strength beyond it. The changes in higher fields are dominantly influenced just by such particles that also show non-linear behavior in the increased range; for example a particle Y. With e.g., three different particles X, Y, and Z differing in their behaviors or saturation behaviors that are non-linear with respect to their field strength, a conclusion can be drawn on the quantitative composition and on an association with a unique ID from the measurements at different field strengths.

Such a measurement can take place as a simplest example by a measurement signal recording during a sinusoidal magnetic field increasing linearly in amplitude. Other ramp functions are equally possible as are other field functions that differ from a sine. A variation of the frequency analog to the variation of the magnetic field strength can equally be used to generate a unique ID. In general, the non-linear magnetic response of particles with a suitable variation of physical parameters such as diameter, material composition, etc. differs in its amplitude and phase progression on excitation at different frequencies. If, for example, different particles X, Y, and Z are combined into a system, this combination can be adapted such that the measurement signal is determined by the individual particles at different frequencies with different weighting amounts and conclusions can thus be drawn on the composition and a unique ID can be assigned. The variation of the frequencies can either take place in successive measurements or can be varied continuously during one measurement. It is possible to acquire the association of a unique ID from a combination of frequency and amplitude variation. In this process, the amplitude and the frequency are simultaneously varied, either in successive measurements or continuously during one measurement. An association with a unique ID is acquired from the measurement signal.

A further preferred variant of the method in accordance with the invention is characterized in that the plurality of magnetic nanoparticles comprises at least two, preferably at least three, types of magnetic nanoparticles that differ from one another at least in their (non-linear) magnetization behavior in an applied magnetic field and/or in their saturation magnetization, in that a static of time variable offset field is additionally applied within step b), and in that the magnetic field strength of the magnetic field and/or the frequency of the magnetic field is varied within step b).

It is here a combination of the previously named measurement approaches 1, 2, and 3. An offset field can thus be switched in a suitable manner during the amplitude and/or frequency variation of the magnetic field. If different frequency measurements are simultaneously combined, the particles acts as frequency mixers in a magnetic field due to their non-linear behavior. In this case, those frequency portions of the measurement signal at the mixer frequency that ideally differ by a suitable choice of the frequencies of the higher harmonic of the individual particles can also additionally be used for the generation of the unique ID.

The magnetic supraparticles used can preferably also have further properties detectable by different methods, e.g., optical properties such as fluorescence, in addition to their special magnetic properties. A combination of a plurality of these "multimodal" properties can thus also be used for the generation of a unique ID.

In accordance with a further preferred variant of the method in accordance with the invention, at least some of the nanoparticles of the plurality of magnetic nanoparticles are each surface modified with chemical groups. The chemical groups here are preferably selected from the group consisting of organic acids, in particular citric acid; silanes, in particular octyltriethoxysilane; polycarboxylate ethers, and mixtures thereof.

The surface modification of the nanoparticles influences the magnetic properties or the magnetic moment of the supraparticles. Due to the surface modification of at least some of the nanoparticles of the plurality of magnetic nanoparticles, changed distances of the nanoparticles from one another occur when they are interassociated to one supraparticle. Different interactions result therefrom that are dependent on the modification and that result in a modification of the characteristic signals. The number of characteristic distinguishable spectra and thus of "codes" can be further increased in this manner.

It is further preferred that the plurality of magnetic nanoparticles comprise a plurality of types of magnetic nanoparticles that differ from one another in their surface modification. The number of characteristic distinguishable spectra and thus of "codes" can be further increased in this manner.

A further preferred variant of the method in accordance with the invention is characterized in that at least some (i.e., at least a plurality) of the nanoparticles of the plurality of magnetic nanoparticles each comprise a core and a shell surrounding the core. The shell here preferably consists of a different material than the core consists of. The shell particularly preferably comprises a material that is selected from the group consisting of silica; polymers, for example polymethylmethacrylate, polystyrene, polyethylene glycol; metal oxides, for example titanium dioxide; and mixtures thereof. The shell can have a variable thickness.

The structure of the nanoparticles influences the magnetic properties or the magnetic moment of the supraparticles. The number of characteristic distinguishable spectra and thus of "codes" can thus be further increased by the use of nanoparticles having said core-shell structure.

It is further preferred that the plurality of magnetic nanoparticles comprise a plurality of types of magnetic nanoparticles that each comprise a core and a shell surrounding the core and that differ from one another at least with respect to the material of the shell. The number of characteristic distinguishable spectra and thus of "codes" can be further increased in this manner.

A further preferred variant of the method in accordance with the invention is characterized in that at least some, preferably all, of the nanoparticles of the plurality of magnetic nanoparticles are assembled into hierarchical substructures within the magnetic supraparticle. The hierarchical substructures are here preferably selected from the group consisting of clusters, spheres, rods, and mixtures and combinations thereof. The magnetic nanoparticles can, for example, first be assembled in clusters/rods. They are already supraparticles that could be used for the ID generation, but are then agglomerated into larger supraparticles. The (sub)structural arrangement, i.e., the use of nanoparticles having hierarchical substructures likewise has the result that the number of characteristic, distinguishable spectra, and thus of "codes", are further increased.

In accordance with a further preferred variant of the method in accordance with the invention, the magnetic supraparticles contain further nanoparticles, preferably diamagnetic nanoparticles and/or paramagnetic nanoparticles, in addition to the plurality of magnetic nanoparticles. The further nanoparticles are non-magnetic nanoparticles. In this respect, diamagnetic nanoparticles and paramagnetic particles are understood as non-magnetic nanoparticles. The magnetic supraparticles can comprise the plurality of magnetic nanoparticles and the further nanoparticles. Alternatively, the magnetic supraparticles can also consist of the plurality of magnetic nanoparticles.

A further variant of the method in accordance with the invention is characterized in that the magnetic supraparticles each have a shell that surrounds the magnetic supraparticles, with the shell preferably
- having a thickness of 1 nm to 10 µm; and/or
- comprising or consisting of a material that is selected from the group consisting of silica; polymers, for example polymethylmethacrylate, polystyrene, polyethylene glycol; metal oxides, for example titanium dioxide; and mixtures thereof; and/or
- being designed as a coating.

A further variant of the method in accordance with the invention is characterized in that the magnetic supraparticles each have pores having a pore size between 1 nm and 60 nm, preferably having a pore size between 7 mm and 12 mm, with the pores being infiltrated with a polymer. The pore size can be determined, for example, by means of gas adsorption, in particular by means of nitrogen adsorption.

With respect to the introduction of the magnetic supraparticles into any desired object or into a matrix of such an object, for example a polymer (e.g., in the marking of plastic objects, adhesives, etc.), it is advantageous to be able to exclude matrix effects. It has been found that a penetration of the matrix material into the supraparticle structure possibly causes signal-changing effects on an MPS measurement. To avoid such signal-changing effects, the magnetic supraparticles can be modified, for example by providing (e.g., coating) the magnetic supraparticles with a shell (e.g., having a thickness of 1 nm to 10 µm and/or of silica or polymer) and/or by infiltration or filling in of the pore spaces of the particles with a polymer. The described penetration of the matrix material can be prevented in this manner. The modified particles are thus inert and indifferent with respect to embedding matrixes of objects in which the magnetic supraparticles should be used.

A further preferred variant of the method in accordance with the invention is characterized in that the magnetic supraparticles are exposed, subsequent to step d), to at least one mechanical influence, preferably a mechanical pressure and/or a shear, by which the magnetic moment of the magnetic supraparticles is changed, subsequently steps b) and c) are repeated, and subsequently thereto the change of the magnetic moment of the magnetic supraparticles is detected with reference to the comparison between the spectra generated in the first step c) and in the second step c).

In accordance with this preferred variant of the method, the magnetic supraparticles can be used as mechanical sensors for the detection of mechanical environmental influences. In this process, the magnetic supraparticles are first measured in accordance with steps a) to d) of the method in accordance with the invention so that a starting value is obtained at which no mechanical environmental influences are present. If now afterward specific mechanical environmental influences such as mechanical pressure or shear act on the magnetic supraparticles that can also result in a complete or partial destruction and/or modification of the composition and/or structure of the magnetic supraparticles, this results in a change of the magnetic properties and thus of the magnetic moment of the magnetic supraparticles. The signal measured by the MPS and the spectrum obtained thus also change due to mechanical environmental influences. If thus steps b) and c) are repeated after the effect of the mechanical environmental influences, a spectrum is obtained that differs from the spectrum that was obtained in the first performance of step c). A conclusion can be drawn on the presence of a mechanical environmental influence due to this difference. In other words, mechanical environmental influences are thus detected by the method, with the magnetic supraparticles acting as a sensor in this process. In this manner, for example, a wear, damage, or improper treatment of objects provided with the magnetic supraparticles can also be detected or demonstrated.

In this variant of the method in accordance with the invention, hollow spheres are preferably used as the magnetic supraparticles or at least as some of the magnetic supraparticles. This has the advantage that, for example, due to mechanical pressure or shear forces on the hollows spheres, the structure of the latter can easily be changed. These structural changes in the hollow spheres have a direct effect on the recorded measurement signal of the MPS or MPI measurement. A conclusion can thus be directly drawn on the, for example, mechanical influence on the hollow spheres from the recorded measurement signal and its changes. The hollow spheres therefore act as a detector for mechanical influences, for example. A "storage effect" moreover additionally results from the irreversible changes of the structure of the hollow spheres, i.e., mechanical effects or shear forces that have acted on the hollow spheres prior to the actual MPS or MPI measurement and that have changed their structure in so doing are detected and read in the later measurements. The mechanical properties of the hollow spheres can also be coordinated exactly and very finely, for example by setting the wall thickness and the strength of the shell. Detectors respectively adapted to the mechanical influences to be expected can thus be manufactured.

Furthermore, the above-described signal-changing effects in an MPS measurement that are caused by the penetration of matrix material into the supraparticle structure can also be used to detect the penetration e.g., of liquids, gases, or other materials into the regions of an object marked by supraparticles and thus to deliver the demonstration of further environmental influences on the object.

In accordance with a particularly preferred variant of the method in accordance with the invention, the magnetic supraparticles are provided in step a) in that at least one object is provided that contains the magnetic supraparticles, with the at least one object preferably being selected from the group consisting of plastic objects, metal objects, ceramic objects, glass objects, and mixtures and combinations thereof, with the at least one object particularly preferably being selected from the group consisting of domestic appliances, clothing, electric devices, vehicles, pharmaceutical products, and mixtures and combinations thereof. As a result, the at least one object can thus also be detected and/or identified by the detection and/or identification of the magnetic supraparticles. A method for the detection and/or identification of objects thus results. The magnetic supraparticles thus serve as a type of marker with which an object can be marked to be able to later detect and/or identify it again with reference to the marker.

A particularly preferred variant of the method in accordance with the invention is characterized in that the magnetic supraparticles are integrated into the material of the at least one object. In other words, the magnetic supraparticles are not only applied onto the at least one object at the surface, but are also introduced into the matrix of the at least one object. In this manner, the supraparticles can no longer be easily removed from the object or destroyed. In contrast to this, markers applied to the object at the surface can easily be removed or destroyed.

The magnetic supraparticles can, for example, be embedded into the object or into the matrix of the object at a specific concentration, e.g., 0.00001 wt % to 10 wt %, preferably 0.0001 wt % to 1 wt %, particularly preferably 0.001 wt % to 0.1 wt %, very particularly preferably 0.001 wt % to 0.01 wt %. In this respect, all the embedding processes are conceivable that embed particles into a surrounding matrix, for example the embedding by means of injection molding, stirring, shaking, mixers, and/or extruders.

In a particularly preferred variant, the method in accordance with the invention is a method for the detection and/or identification of objects containing magnetic supraparticles by means of magnetic particle spectroscopy or magnetic particle imaging, wherein in step a) at least one object is provided that contains the magnetic supraparticles. In this process, the at least one object is preferably selected from the group consisting of plastic objects, metal objects, ceramic objects, glass objects, and mixtures and combinations thereof, wherein the at least one object is particularly preferably selected from the group consisting of domestic appliances, clothing, electric devices, vehicles, pharmaceutical products, and mixtures and combinations thereof. It is particularly preferred that the magnetic supraparticles are integrated into the material of the at least one object. In other words, the magnetic supraparticles are not only applied onto the at least one object at the surface, but are also introduced into the matrix of the at least one object.

The present invention also relates to the use of the method in accordance with the invention for the detection and/or identification of objects. In this respect, the objects are preferably selected from the group consisting of plastic objects, metal objects, ceramic objects, glass objects, and mixtures and combinations thereof, wherein the objects are particularly preferably selected from the group consisting of domestic appliances, clothing, electric devices, vehicles, pharmaceutical products, and mixtures and combinations thereof. It is particularly preferred here that the magnetic supraparticles are integrated into the material of the objects. In other words, the magnetic supraparticles are not only applied to the objects at the surface, but are also embedded in the matrix of the objects.

The present invention will be explained in more detail with reference to the following Figures and examples without restricting it to the specific embodiments and parameters shown here.

In FIG. 1, a schematic representation of an exemplary magnetic supraparticle is shown such as can be used in the method in accordance with the invention. The magnetic supraparticle contains a plurality of magnetic nanoparticles having different sizes and different shapes. These magnetic nanoparticles are assembled into the magnetic supraparticle that as a result has a specific composition and structure.

Figure 2:
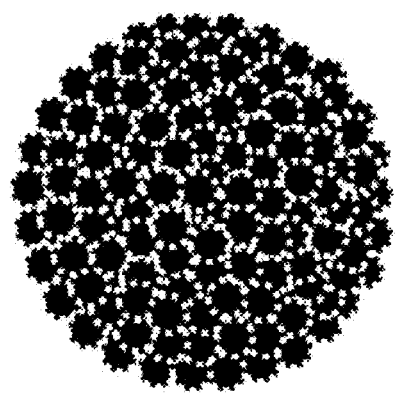
FIG. 2 illustrates a further exemplary magnetic supraparticle that can be used in the method in accordance with an aspect of the invention, wherein the magnetic nanoparticles that are contained in the magnetic supraparticle are surface modified with chemical groups.

In FIG. 2, a schematic representation of a further exemplary magnetic supraparticle is shown such as can be used in the method in accordance with the invention. In this respect, the magnetic nanoparticles that are contained in the magnetic supraparticle are surface modified with chemical groups. The magnetic nanoparticles are shown in black in FIG. 2, whereas the surface modification is shown as a white dashed line. The magnetic supraparticle itself can also have a surface modification.

Figure 3:
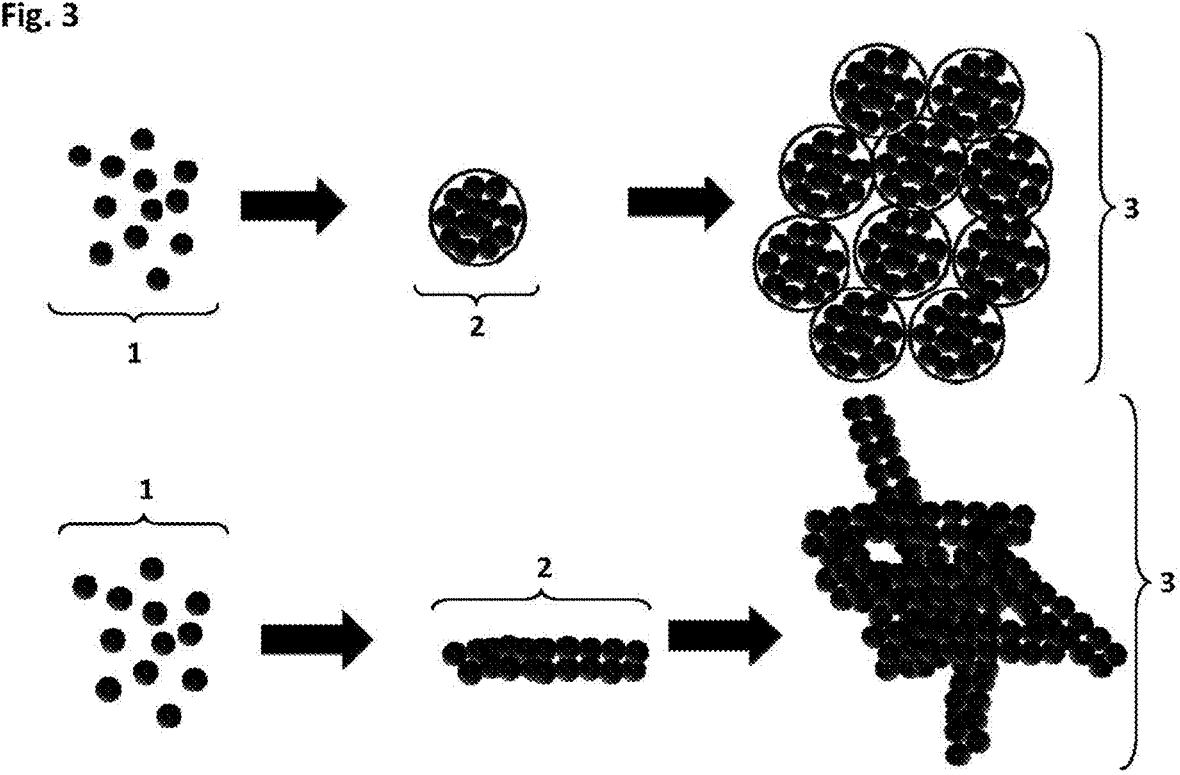
FIG. 3 illustrates an assembly of two further exemplary supraparticles in accordance with an aspect of the invention, wherein individual magnetic nanoparticles 1 are first assembled to form a superstructure 2 in the first step, and in a second step, an agglomeration of the respective superstructure 2 to form the magnetic supraparticle 3 then takes place. Finally, the plurality of magnetic nanoparticles are assembled to form hierarchical substructures within the magnetic supraparticle.

In FIG. 3, a schematic representation of the assembly of two further exemplary supraparticles is shown such as can be used in the method in accordance with the invention. In this respect, individual magnetic nanoparticles 1 are first assembled to form a superstructure 2 in the first step. In the example shown in the upper part of the Figure, a spherical superstructure is obtained, whereas in the example shown in the lower part of the Figure, a rod-shaped superstructure is obtained. In a second step, an agglomeration of the respective superstructure 2 to form the magnetic supraparticle 3 then takes place. Finally, the plurality of magnetic nanoparticles are assembled to form hierarchical substructures within the magnetic supraparticle. The respective superstructures 2 or substructures are actually already supraparticles that can be used for the ID generation. However, due to the agglomeration of a plurality of (different) superstructures, a still larger supraparticle can be generated and an even more characteristic signal can thereby be generated.

Figure 4:
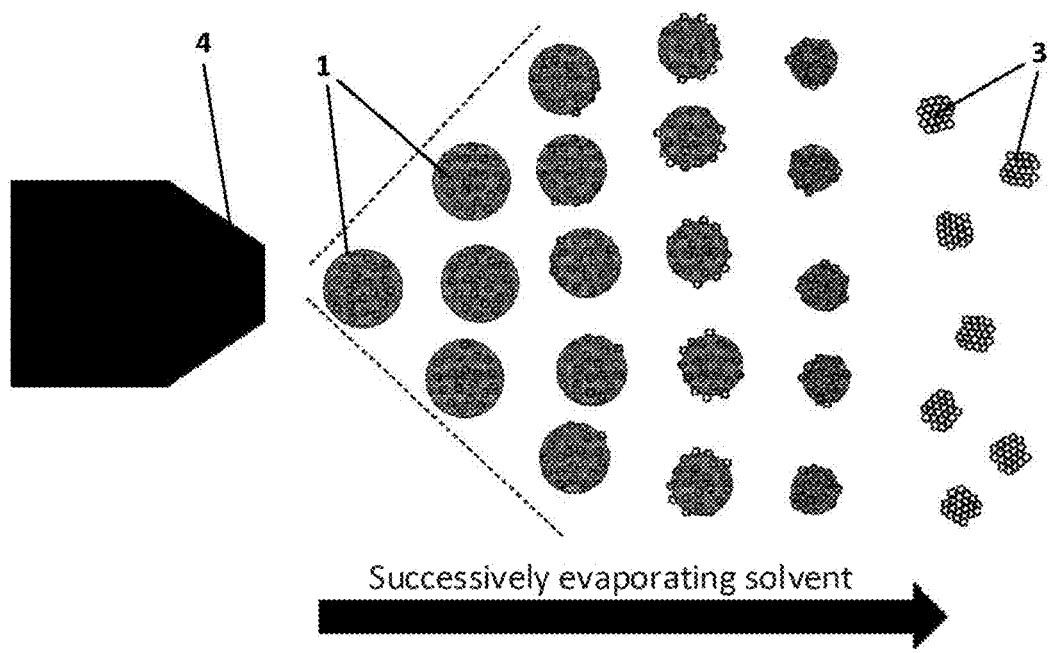
FIG. 4 illustrates a method of manufacture of supraparticles in accordance with an aspect of the invention by spray drying.

In FIG. 4, a possible manufacture of the supraparticles used in the method in accordance with the invention by means of spray drying is schematically shown. In this respect, magnetic nanoparticles 1 are assembled to form the magnetic supraparticles 3. For this purpose, the magnetic nanoparticles 1 are sprayed in dispersion as fine (1 μm to 10 μm) droplets from an atomizer nozzle 4 into a sample chamber. Due to an increased temperature in the sample chamber, the solvent, e.g., water, successively evaporates and the individual magnetic nanoparticles 1 agglomerate into magnetic supraparticles 3.

Figure 5:
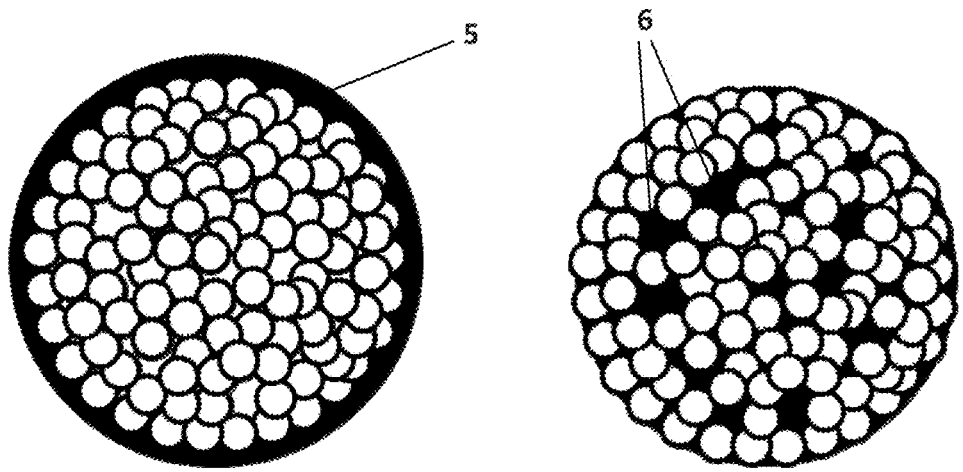
FIG. 5 illustrates two further magnetic supraparticles that can be used in the method in accord with an aspect of the invention. In the left, the magnetic supraparticle has a shell 5 that surrounds the magnetic supraparticle. In the right, the magnetic supraparticle has pores that are infiltrated with a polymer 6.

In FIG. 5, schematic representations of two further exemplary magnetic supraparticle are shown such as can be used in the method in accordance with the invention. In the left part of the Figure, the magnetic supraparticle has a shell 5 that surrounds the magnetic supraparticle. The penetration of another matrix material, e.g., the material of an object in which the magnetic supraparticles are contained, is prevented by the shell. The shell 5 can have a thickness of 1 nm to 10 μm and/or can comprise or consist of a material that is selected from the group consisting of silica; polymers, for example polymethylmethacrylate, polystyrene, polyethylene glycol; metal oxides, for example titanium dioxide; and mixtures thereof, and/or can be designed as a coating. In the right part of the Figure, the magnetic supraparticle has pores (e.g., having a pore size of 1 nm to 60 nm, or having a pore size between 7 nm and 12 nm), with the pores being infiltrated or filled in with a polymer 6. The penetration of another matrix material, e.g., the material of an object in which the magnetic supraparticles are contained, is prevented by the infiltration or filling in of the pores.

EMBODIMENTS

Different options for the creation of a characteristic signal will be explained and exemplary signal progressions shown in the following.

1) Assembly of the Substructures and Signal Progression Determination

As already shown in FIG. 3, a particularly characteristic signal can be achieved by the assembly to form a superstructure or substructure.

Figure 6:
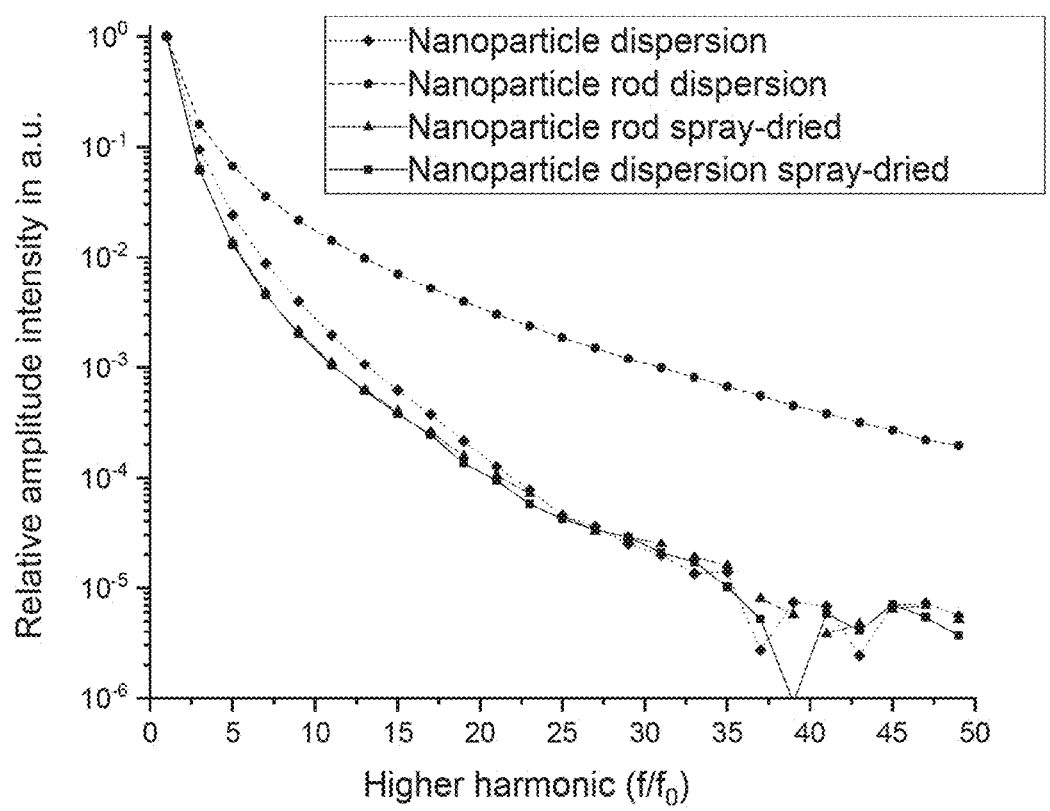
FIG. 6 depicts the amplitude spectra and the phase spectra of four different samples determined by MPS, wherein the relative amplitude intensity is plotted against the higher harmonic.
Figure 7:
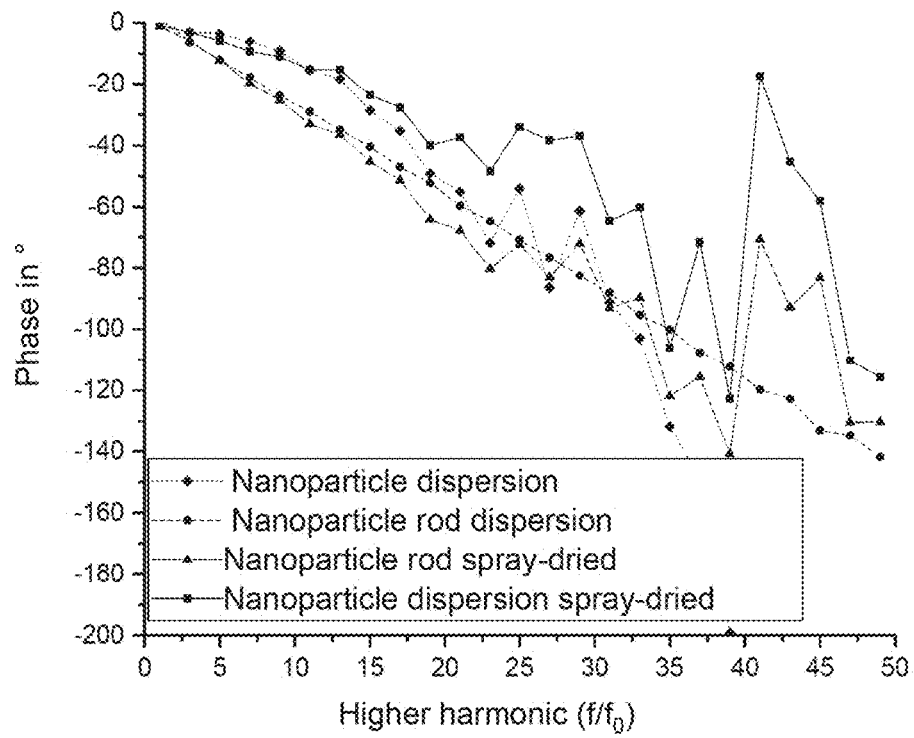
FIG. 7 depicts the amplitude spectra and phase spectra of four different samples determined by MPS, wherein the phase is plotted against the higher harmonic.

This is illustrated in FIG. 6 and FIG. 7 in which amplitude spectra and phase spectra of four different samples determined by MPS are shown. In the amplitude spectra shown in FIG. 6, the relative amplitude intensity is entered against the higher harmonic. In the phase spectra shown in FIG. 7, the phase is entered against the higher harmonic.

The graph marked by the dotted line and the diamond symbols in FIG. 6 and FIG. 7 shows the respective spectrum of magnetic nanoparticles that are present in a dispersion. The graph marked by the solid line and the square symbols in FIG. 6 and FIG. 7 shows the respective spectrum of the same magnetic nanoparticles that were, however, assembled by means of spray drying into magnetic supraparticles such as can also be used in the method in accordance with the invention. The graph marked by the dashed line and the circle symbols in FIG. 6 and FIG. 7 in turn shows the respective spectrum of the same magnetic nanoparticles that are, however, present assembled into rod-shaped superstructures. These superstructures are basically already magnetic supraparticles such as can be used in the method in accordance with the invention. The graph marked by the chain-dotted line and the triangle symbols in FIG. 6 and FIG. 7 finally shows the respective spectrum of the same magnetic nanoparticles that were, however, this time first assembled into rod-shaped supraparticles that were subsequently assembled into magnetic supraparticles by means of spray drying. With these magnetic supraparticles, the magnetic nanoparticles are thus assembled into hierarchical substructures—in the form of rods—within the magnetic supraparticle.

The signal progression can be changed by the assembly of the individual nanoparticles (dotted line, diamond symbol) into rod-shaped superstructures (dashed line, circle symbol). This assembly is already a supraparticle that can be used for object marking. If the rod-shaped superstructures are combined into even larger particles, for example by means of spray drying (chain dotted line, triangle symbol), the signal can in turn be varied. The then resulting amplitude intensity signal (solid line, rectangle symbol) is almost identical to the spray drying of the original nanoparticles. However, the two curves differ with respect to their phases in dependence on the higher harmonic, as can be recognized in FIG. 7. These differences are in particular significant up to approximately the 20th harmonic. The measurement values then scatter more due to the relatively large measurement error (not shown). It also becomes clear in this example that, for the distinction of the code objects, either the amplitude intensity progressions that are here identical for the last-named samples, or the progression of the phase can be used, or a combination of the two.

Figure 8:
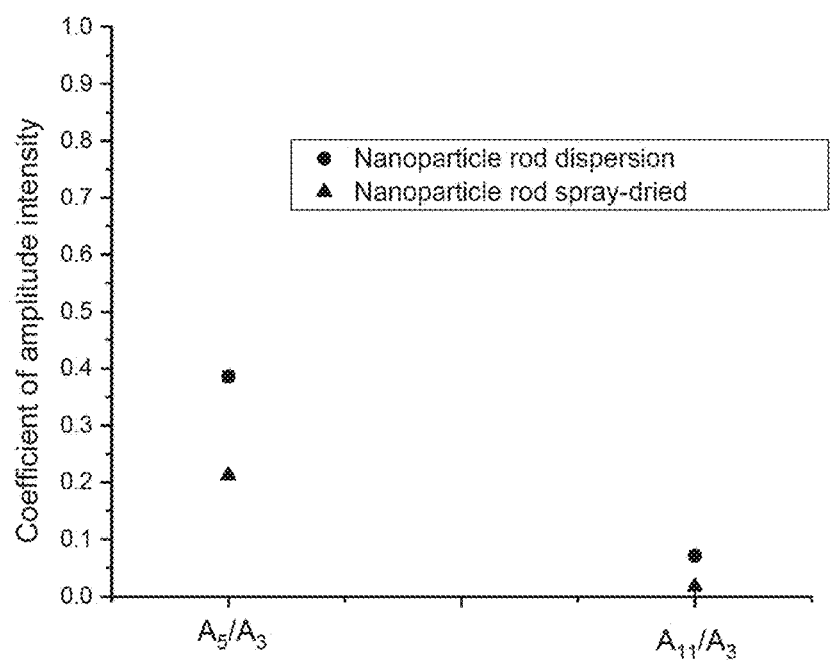
FIG. 8 depicts the quotients of the amplitude intensity of different harmonics with respect to one another for two samples, i.e., for the nanoparticles assembled into rod-shaped superstructures (dashed line, circle symbol) and for the nanoparticles first assembled into rod- shaped superstructures and subsequently agglomerated into magnetic supraparticles having a substructure by means of spray drying (chain-dotted line, triangle symbol).

In FIG. 8, quotients of the amplitude intensity of different harmonics are graphically shown with respect to one another for two of the already above-named samples, namely for the nanoparticles assembled into rod-shaped superstructures (dashed line, circle symbol) and for the nanoparticles first assembled into rod-shaped superstructures and subsequently agglomerated into magnetic supraparticles having a substructure by means of spray drying (chain-dotted line, triangle symbol). The fivefold excitation frequency ($A_5$) divided by the threefold excitation frequency ($A_3$) and the elevenfold excitation frequency ($A_{11}$) divided by the threefold excitation frequency ($A_3$) are shown by way of example here. The two different samples can be described and identified with the aid of the coefficients calculated in this manner. It can be seen here that the two named samples have different values of the relationships. The error bars of the respective coefficients are shown, but are so small that they cannot be recognized. The quotient $A_5/A_3$ here describes the (negative) pitch of the respective measurement curves between the third and fifth harmonics, while $A_{11}/A_3$ describes the (negative) pitch of the respective measurement curves between the eleventh and third harmonics. The progressions of different measurement curves can be described by coefficients calculated in this manner. For a more exact description of the curve progression, mathematical models can be used and all the measurement points can, for example, be put into relationship with one another. In addition to the amplitude coefficients thus acquired, the measurement values of the phase can be used in dependence on the harmonic for the signal setting and the detection.

2) Variation of the Type of Assembly

An assembly of the individual nanoparticles to form supraparticles can take place by drying thereof. The individual nanoparticles agglomerate or aggregate due to the evaporation of the solvent and form supraparticles. Characteristic signals with respect to the phase (FIG. 9) or to the amplitude intensity (FIG. 10) can be generated by different drying variations of the suspension (diamond, dotted representation) such as furnace drying, (circle, dashed representation) spray drying (rectangle, linear representation) or freeze-drying (triangle, chain-dotted representation). A varying signal can be set by variation of the type of assembly by the arising different interactions.

Figure 9:
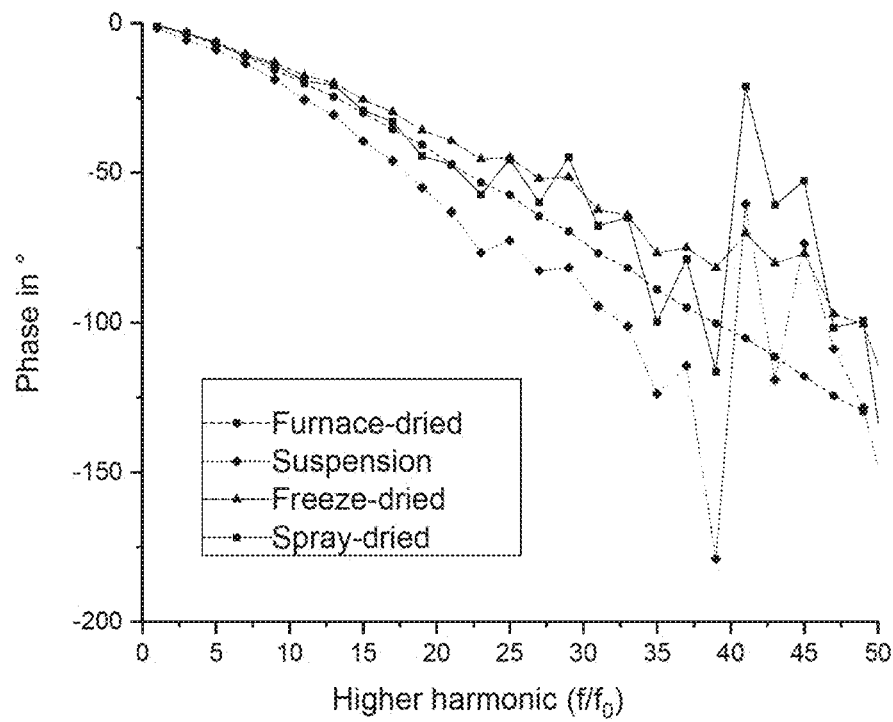
FIG. 9 depicts the phase value against the higher harmonics in the spectra obtained on four different samples.
Figure 10:
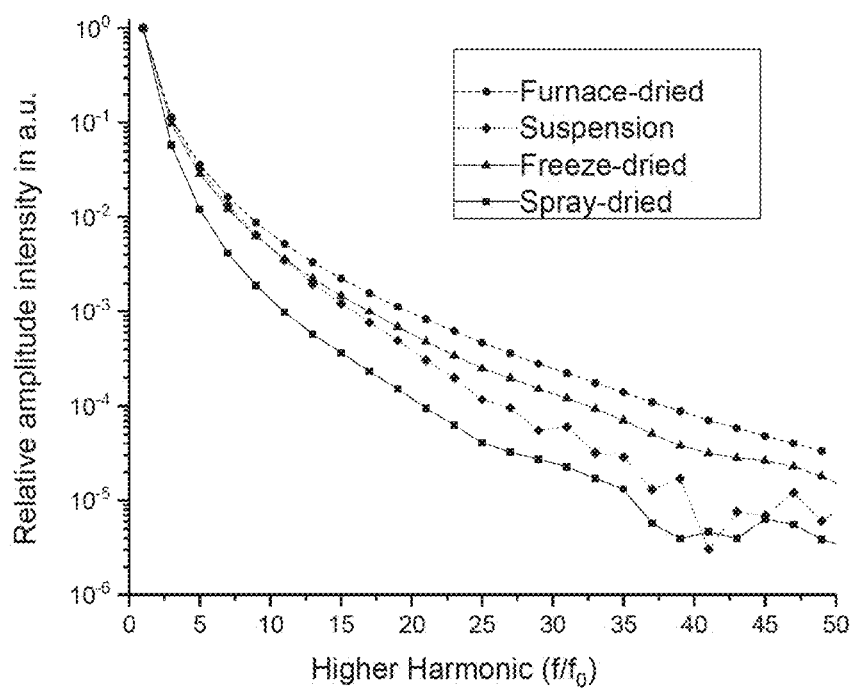
FIG. 10 depicts the relative amplitude intensity against the higher harmonics in the spectra obtained on four different samples.

This is illustrated in FIG. 9 and FIG. 10 in which amplitude spectra and phase spectra of four different samples are shown determined by means of MPS. In the amplitude spectra shown in FIG. 9, the relative amplitude intensity is entered against the higher harmonics. In the phase spectra shown in FIG. 10, the phase is entered against the higher harmonics.

The graph marked by the dotted line and the diamond symbols in FIG. 9 and FIG. 10 shows the respective spectrum of magnetic nanoparticles that are present in a dispersion. The graph marked by the solid line and the square symbols in FIG. 9 and FIG. 10 shows the respective spectrum of the same magnetic nanoparticles that were, however, assembled by means of spray drying into magnetic supraparticles such as can also be used in the method in accordance with the invention. The graph marked by the dashed line and the circle symbols in FIG. 9 and FIG. 10 in turn shows the respective spectrum of the same magnetic nanoparticles that were, however, assembled into magnetic supraparticles by means of furnace drying. These magnetic supraparticles can also be used in the method in accordance with the invention. The graph marked by the chain-dotted line and the triangle symbols in FIG. 9 and FIG. 10 finally shows the respective spectrum of the same magnetic nanoparticles that were, however, assembled into magnetic supraparticles by means of freeze drying. These magnetic supraparticles can also be used in the method in accordance with the invention.

It can be recognized in FIG. 9 and FIG. 10 that due to different manufacturing methods of the magnetic supraparticle in which different respective process parameters, here by way of example different drying parameters of the original suspension, such as furnace drying, freeze-drying, or spray drying are used, different curve progressions of the relative amplitude intensity and different phase progressions can be realized.

3) Surface Modification of the Nanoparticles for Signal Variation

As already discussed with reference to FIG. 2, a particularly characteristic signal can be generated in that the nanoparticles used are surface modified before they are combined into supraparticles.

Figure 11:
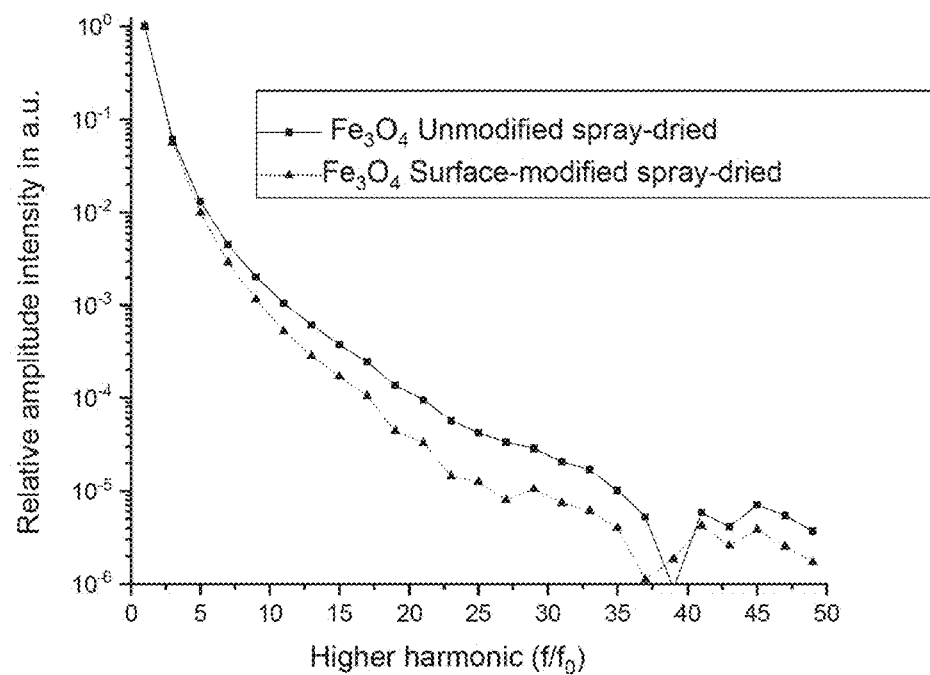
FIG. 11 depicts the relative amplitude intensity against the higher harmonics in the spectra obtained on two different $Fe_3O_4$ samples.

FIG. 11 illustrates this by way of example with reference to the signal progression of the relative amplitude intensity in dependence on the higher harmonic. Non-surface modified iron oxide nanoparticles that have been assembled into magnetic supraparticles by means of spray drying (rectangle symbols, solid line) here show a different signal progression than surface modified iron oxide particles that have been assembled into magnetic supraparticles by means of spray drying (triangle symbols, dotted line). The surface modification takes place in this process by a functionalization with a silane. The phase progressions are not shown, but can also be influenced by surface modification of the nanoparticles.

4) Signal Change of the Code Particles by Environmental Influences

It is possible that the characteristic signal of the magnetic supraparticles varies due to their environment. This is shown by way of example in FIG. 12 in which signal progressions of the relative amplitude intensity are shown in dependence on the higher harmonic for three different samples. The signal of a sample of magnetic supraparticles usable in the method in accordance with the invention (original signal; square symbol, solid line), the signal of a sample in which the same magnetic supraparticles are embedded in polyethylene glycol (triangle signal, dotted line), and the signal of a sample in which the same magnetic supraparticles are embedded in paraffin wax are compared here.

Figure 12:
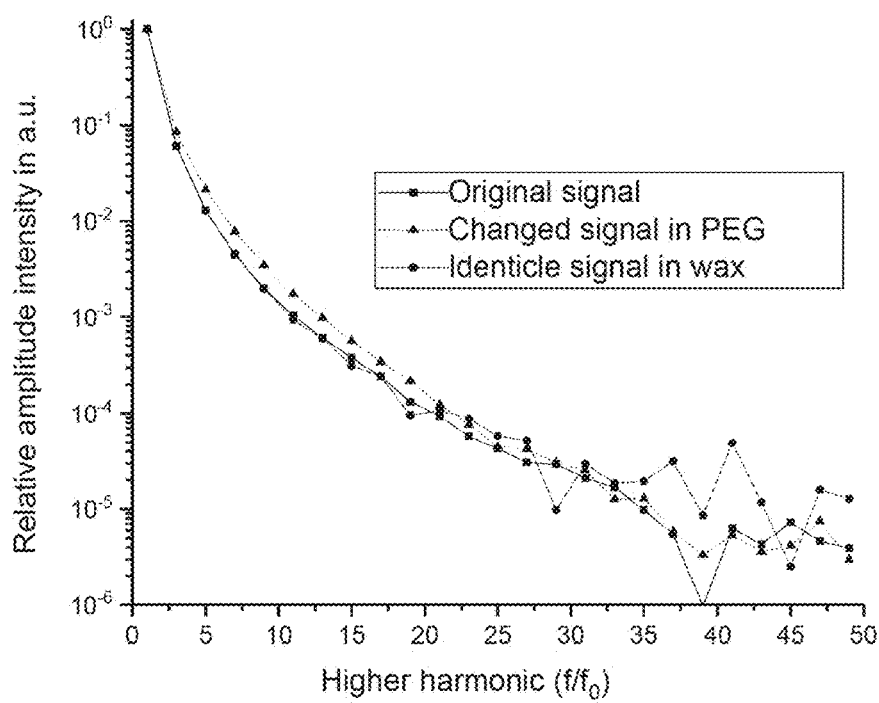
FIG. 12 depicts the signal progressions of the relative amplitude intensity on the dependence on the higher harmonic for three different samples, wherein the original signal is represented by the square symbol and solid line, the signal of a sample in which the same magnetic supraparticles are embedded in polyethylene glycol represented by the triangle symbol and dotted line, and the signal of a sample in which the same magnetic supraparticles are embedded in paraffin wax are shown by the filled circle symbol and the dotted line.

It can be recognized in FIG. 12 that the characteristic signal of the untreated magnetic supraparticles changes by embedding in polyethylene glycol, whereas the signal remains unchanged on embedding in paraffin wax. The structure of the supraparticles can be changed in dependence on process parameters such as mechanical strain, interaction with the environment, viscosity of the matrix, or similar, which results in a changed magnetic signal. The particles were embedded at a concentration of approximately 1 wt % using a vortexer of Heathrow Scientific into the matrices shown here by shaking at 1000 r.p.m. for 2 min. This change of the signal can be prevented by a skillful sample preparation or can also be deliberately used to change the code.

Figure 13:
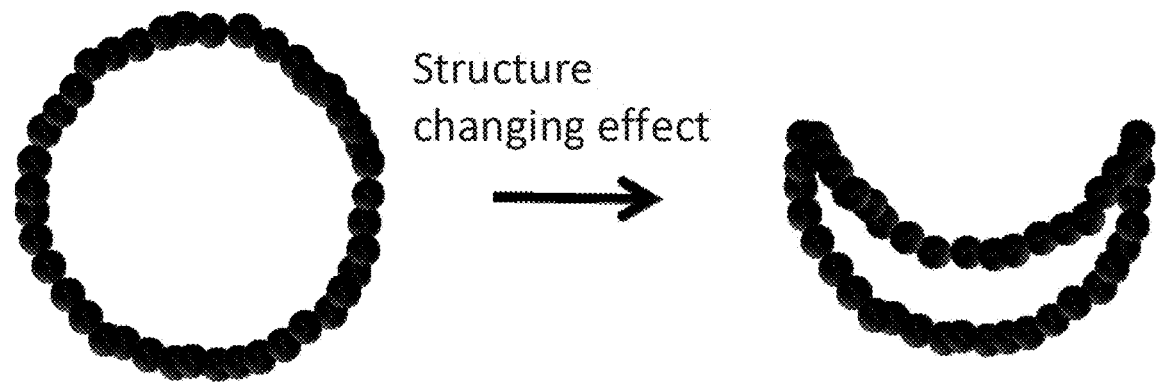
FIG. 13 depicts a structural change in a hollow sphere supraparticle that can be detected by the use of the supraparticles and their multiple measurement by MPS or MPI in accordance with an aspect of the invention.

Structural changes can also be detected by the use of the supraparticles and their multiple measurement by MPS or MPI. The structure of the supraparticles changes by structure changing influences such as mechanical strain. This structural change is illustrated by way of example for hollow sphere supraparticles in FIG. 13. The hollow structure can be (partially) changed, for example. The structural change then results in a change of the detected signal in the MPS or MPI. By a multiple measurement after different structural changes, the latter can be detected and conclusions can be drawn on environmental effects such as acting mechanical strain by a skillful adaptation of the supraparticles.

Figure 14:
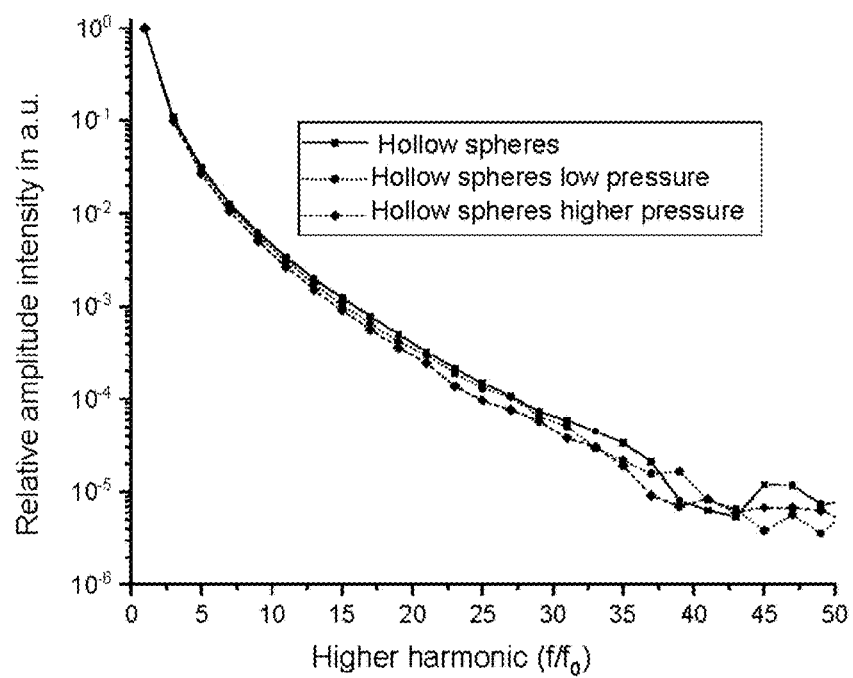
FIG. 14 depicts a change the relative amplitude intensity as a function the higher harmonic resulting from a drop in pressure, in accordance with an aspect of the invention.

This signal change is shown by way of example for pressure forces of different strengths in FIG. 14. As the pressure on the originally intact hollow spheres increases, the relative amplitude intensity over the higher harmonics drops faster. A change of the phase by the structure changing effects is also conceivable, but not shown here.

The invention claimed is:

1. A method for detecting and/or identifying magnetic supraparticles by magnetic particle spectroscopy or by magnetic particle imaging, in which
   (a) magnetic supraparticles are provided that each contains a plurality of magnetic nanoparticles and has a specific composition and/or structure,
   (b) the magnetic supraparticles are exposed to at least one magnetic field, wherein at least one voltage and/or voltage progression is/are induced in dependence on the magnetic moment of the magnetic supraparticles, with the at least one voltage and/or the voltage progression being detected as at least one measurement signal,
   (c) at least one spectrum is generated from said at least one measurement signal, which spectrum contains higher harmonics each having an amplitude and a phase, and
   (d) the magnetic supraparticles are detected and/or identified with reference to the at least one generated spectrum,
   wherein the plurality of magnetic nanoparticles comprises a plurality of types of magnetic nanoparticles that differ from one another at least in basic shape, and/or that differ from one another at least in material, wherein the composition and/or structure of the magnetic supraparticles are fixed such that a specific characteristic spectrum or a series of specific characteristic spectra are obtained by magnetic particle spectroscopy or magnetic particle imaging.

2. The method in accordance with claim 1, wherein the detecting and/or identifying of the magnetic supraparticles in step (d) takes place with reference to a progression of the phases of the higher harmonics of the at least one spectrum and/or with reference to relative relationships of intensities of the amplitudes of the higher harmonics of the at least one spectrum.

3. The method in accordance with claim 1, wherein:

the magnetic supraparticles each has a particle size of 50 nm to 150-µm; and/or the magnetic nanoparticles of the plurality of magnetic nanoparticles each has a particle size of 1 nm to 100 nm.

4. The method in accordance with claim 1, wherein the magnetic nanoparticles of the plurality of magnetic nanoparticles each has a basic shape that is selected from a spherical basic shape, an octahedral basic shape, an ellipsoid basic shape, a rod-shaped basic shape, a cylindrical basic shape, and a cubic basic shape.

5. The method in accordance with claim 1, wherein the nanoparticles of the plurality of magnetic nanoparticles each comprises a material that is selected from the group consisting of ferromagnetic materials, ferrimagnetic materials, superparamagnetic materials, and mixtures thereof.

6. The method in accordance claim 1, wherein the plurality of magnetic nanoparticles comprise at least two types of magnetic nanoparticles that differ from one another at least in their saturation magnetization and in that a static or time variable offset field is additionally applied within step (b).

7. The method in accordance with claim 1, wherein the plurality of magnetic nanoparticles comprise at least two types of magnetic nanoparticles that differ from one another at least in their magnetization behavior in an applied magnetic field and/or in their saturation magnetization; and in that the magnetic field strength of the at least one magnetic field and/or the frequency of the at least one magnetic field and/or the frequency of the magnetic field is varied within step (b).

8. The method in accordance with claim 1, wherein at least some of the nanoparticles of the plurality of magnetic nanoparticles are each surface modified by chemical groups.

9. The method in accordance with claim 8, wherein the chemical groups are provided by reacting the magnetic nanoparticles with a compound selected from the group consisting of organic acids, silanes, polycarboxylate ethers, and mixtures thereof.

10. The method in accordance with claim 8, wherein the plurality of magnetic nanoparticles comprise a plurality of types of magnetic nanoparticles that differ from one another in their surface modifications.

11. The method in accordance with claim 1, wherein at least some of the nanoparticles of the plurality of magnetic nanoparticles each comprises a core and a shell surrounding the core.

12. The method in accordance with claim 11, wherein the plurality of magnetic nanoparticles comprise a plurality of types of magnetic nanoparticles that each comprises a core and a shell surrounding the core and that differs from one another at least with respect to the material of the shell.

13. The method in accordance with claim 1, wherein at least some of the nanoparticles of the plurality of magnetic nanoparticles are assembled into hierarchical substructures within the magnetic supraparticles.

14. The method in accordance with claim 1, wherein the magnetic supraparticles additionally contain non-magnetic nanoparticles.

15. The method in accordance with claim 1, wherein the magnetic supraparticles each has a shell that surrounds the magnetic supraparticle.

16. The method in accordance with claim 1, wherein the magnetic supraparticles each has pores having a pore size of 1 nm to 60 nm, with the pores being infiltrated with a polymer.

17. The method in accordance with claim 1, wherein the magnetic supraparticles are exposed, subsequent to step (d), to at least one mechanical influence by which the magnetic moment of the magnetic supraparticles is changed, subsequently steps (b) and (c) are repeated, and subsequently thereto the change of the magnetic moment of the magnetic supraparticles is detected with reference to the comparison between the at least one spectrum respectively generated in the first step (c) and in the second step (c).

18. The method in accordance with claim 1, wherein the magnetic supraparticles are provided in step (a) in that at least one object is provided that contains the magnetic supraparticles.

19. The method in accordance with claim 1, wherein magnetic supraparticles are present in an object selected from the group consisting of plastic objects, metal objects, ceramic objects, glass objects, and mixtures and combinations thereof.

* * * * *